United States Patent [19]

Mederski et al.

[11] Patent Number: 5,684,015
[45] Date of Patent: Nov. 4, 1997

[54] IMIDAZOPYRIDINES AS PHARMACEUTICAL AGENTS

[75] Inventors: Werner Mederski, Erzhausen; Matthias Osswald, Zwingenberg; Pierre Schelling, Mühltal; Klaus-Otto Minck; Dieter Dorsch, both of Ober-Ramstadt; Norbert Beier, Reinheim; Ingeborg Lues, Darmstadt, all of Germany

[73] Assignee: Merck Patent Gesellschaft mit Beschrankter Haftung, Darmstadt, Germany

[21] Appl. No.: 528,305

[22] Filed: Sep. 14, 1995

[30] Foreign Application Priority Data

Sep. 15, 1994 [DE] Germany .................. 44 32 860.5

[51] Int. Cl.$^6$ .................. C07D 471/04; A61K 31/435
[52] U.S. Cl. .................. 514/303; 546/118
[58] Field of Search .................. 546/118; 514/303

[56] References Cited

U.S. PATENT DOCUMENTS 5,242,928  9/1993  Mederski .................. 514/303
5,332,744  7/1994  Chakravarty et al. .................. 514/261
5,405,964  4/1995  Mederski et al. .................. 546/118

FOREIGN PATENT DOCUMENTS 0 400 974  12/1990  European Pat. Off. .

*Primary Examiner*—Johann Richter
*Assistant Examiner*—Laura L. Stockton
*Attorney, Agent, or Firm*—Millen, White, Zelano & Branigan, P.C.

[57] ABSTRACT

Described herein are novel imidazopyridine derivatives of the formula I

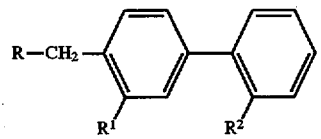

wherein

R is

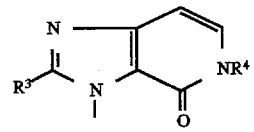

and $R^1$, $R^2$, $R^3$ and $R^4$ are as defined in Patent Claim 1, and their salts, which exhibit antagonistic properties towards angiotensin II and can be used for the treatment of hypertension, aldosteronism, cardiac insufficiency and increased intraocular pressure, and of disorders of the central nervous system.

11 Claims, No Drawings

IMIDAZOPYRIDINES AS PHARMACEUTICAL AGENTS

The invention relates to novel imidazopyridine derivatives of the formula I

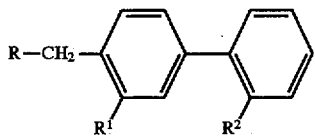

wherein
R is

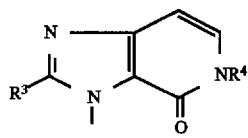

$R^1$ is F, Cl, Br, A or $CF_3$, $R^2$ is —$SO_2NH$—$COR^5$, $R^3$ is A, $C_2$-$C_6$-alkenyl, $C_2$-$C_6$-alkynyl, $C_3$-$C_8$-cycloalkyl-$C_kH_{2k}$- or $C_1$-$C_6$-alkyl, wherein one $CH_2$ group is replaced by O or S, $R^4$ is B, $R^8$, or $C_2$-$C_6$-alkenyl, $C_2$-$C_6$-alkynyl, —$C_nH_{2n}$—$R^9$ or —$CHR^{10}$—$C_kH_{2k}$—$R^{11}$ which is mono- or polysubstituted by COOH, COOA, CN, $NO_2$, $NR^6R^7$, $NHCOR^8$, $NHSO_2R^8$, Hal and/or Ar, $R^5$ is A, —$C_tH_{2t}$-($C_3$-$C_8$-cycloalky), —$C_tH_{2t}$—Ar, —OA, —O—$C_tH_{2t}$-($C_3$-$C_8$-cycloalkyl), —O—$C_tH_{2t}$—Ar, —$C_pH_{2p}$—O-$C_3$-$C_8$-cycloalkyl or —$C_pH_{2p}$—O—Ar, $R^6$ and $R^7$ are each H, A, $C_2$-$C_6$-alkenyl or $C_2$-$C_6$-alkynyl, Ar, $ArC_nH_{2n}$— or $Het^2$, $R^6$ is also —$CH_2COOA$, —$SO_2$—A or —$SO_2$—Ar, $R^6$ and $R^7$ together are also an alkylene chain having 2-5 C atoms, which can be monosubstituted or polysubstituted by carbonyl oxygen, Ar, $Het^2$, —CO—Ar, —COOA, —CO—N(A)$_2$, —$CH_2OH$, —$SO_2$—Ar and/or —NH—CO—A and/or interrupted by O or by —$NR^{16}$—, $R^8$ is $C_1$-$C_5$-alkyl, wherein one or more H atoms can also be replaced by F, $R^9$ is $C_3$-$C_8$-cycloalkyl CN, COOA, COOH, Ar, $Het^1$, $Het^2$, 1H-tetrazol-5-yl, —CO—$NR^6R^7$, —CO—$R^8$, —CO—Ar, —CO—$Het^2$, —CO—$R^{14}$, —C(=$NR^{12}$)—A, —C(=$NR^{12}$)—$Het^2$, —S(O)$_m$—A, —S(O)$_m$—Ar, —S(O)$_m$—$Het^2$, —$SO_2$—NH—$Het^2$ or —$SO_2$—$OR^{15}$, $R^{10}$ is COOH, COOA, $CONR^6R^7$, CN, $NO_2$, $NHCOR^{11}$, $NHSO_2R^{11}$ or 1H-tetrazol-5-yl, $R^{11}$ is Ar or cycloalkyl having 3–8 C atoms, $R^{12}$ is H, OH, CN, $R^{13}$, $OR^{13}$ or OAr, $R^{13}$ is A, $C_2$-$C_6$-alkenyl or $C_2$-$C_6$-alkynyl, $R^{14}$ is —NH—$CHR^{15}$—COOH, —NH—$CHR^{15}$—COOA, —$CH_2S(O)_m$—Ar, —$CH_2$—COOA, —$C_nH_{2n}$—$NO_2$, —$C_nH_{2n}$—$NR^6R^7$ or —$C_nH_{2n}$—NHCOOA, $R^{15}$ is H or A, $R^{16}$ is H, A, Ar, COOA, $Het^2$ or $SO_2$—Ar, A is $C_1$-$C_6$-alkyl, Ar is an unsubstituted phenyl group or a phenyl group monosubstituted or disubstituted by $R^8$, OH, $OR^{11}$, COOH, COOA, $CONH_2$, CONHA, CON(A)$_2$, $CH_2OH$, $CH_2OA$, CN, $NO_2$, $NH_2$, NHA, N(A)$_2$, $NHCOR^{11}$, NHCOOA, $NHSO_2R^8$, Hal and/or 1H-tetrazol-5-yl, $Het^1$ is a five- or six-membered saturated heterocyclic radical having 1 to 3 N, O and/or S atoms, which can be monosubstituted by carbonyl oxygen or =$NR^{12}$ and/or whose ring N atom(s) can in each case be substituted by A or Ar, $Het^2$ is a five- or six-membered heteroaromatic radical having 1 to 3 N, O and/or S atoms, which can also be fused with a benzene or pyridine ring, Hal is F, Cl, Br or I, k and t are each 0, 1, 2, 3 or 4, m is 0, 1 or 2, n is 1, 2, 3, 4, 5 or 6, and p is 1 or 2, and their salts.

Imidazopyridines compounds are known from European Patent Application A2-0400 974.

SUMMARY OF THE INVENTION

An object of the invention was to find novel compounds which can be used for the preparation of drugs.

Upon further study of the specification and appended claims, further objects and advantages of this invention will become apparent to those skilled in the art.

It has been found that the compounds of the formula I and their salts possess very valuable pharmacological properties coupled with a good tolerance. In particular, they exhibit antagonistic properties towards angiotensin II and can therefore be used as pharmaceutical active ingredients for the prophylaxis and/or therapy of coronary, cardiovascular and vascular disorders, in particular for the treatment of angiotensin II-dependent hypertension, aldosteronism, cardiac insufficiency and increased intraocular pressure, and of disorders of the central nervous system, also of hypertrophy and hyperplasia of the blood vessels and of the heart, angina pectoris, cardiac infarct, stroke, restenoses and angioplasty or by-pass operations, arteriosclerosis, glaucomas, macular degeneration, hyperuricaemia, kidney function disorders, e.g. kidney failures, diabetic nephropathy, diabetic retinopathy, psoriasis, angiotensin II-mediated disorders in female reproductive organs, perceptive disorders, e.g. dementia, amnesia, memory function disorders, anxiety states, depression and/or epilepsy.

These effects can be determined by conventional in vitro or in vivo methods such as, for example, those described in U.S. Pat. No. 4,880,804, U.S. Pat. No. 5,036,048 and International Patent Application 91/14367 and also by A. T. Chiu et al., J. Pharmacol. Exp. Therap. 250, 867–874 (1989), and by P. C. Wong et al., ibid. 252, 719–725 (1990; in vivo, on rats).

In particular, these compounds have a high affinity for the $AT_1$ and for the $AT_2$ receptor, which can be detected e.g. on the adrenal medulla of rats according to S. Whitebread et al., Biochem. Biophys. Res. Commun. 163, 284–291 (1989) and according to A. T. Chiu et al., Eur. J. Pharmacol. 170, 117–118 (1989). The compounds additionally show a functional antagonism at the $AT_1$ receptor.

The invention relates to the compounds of the formula I and their salts and to a process for the preparation of these compounds and their salts, characterized in that (a) a compound which corresponds to the formula I but carries an —$SO_2NH_2$— group in place of the radical $R^2$ is reacted with a compound of the formula E—$COR^5$, or (b) a compound of the formula I is freed from one of its functional derivatives by treatment with a solvolysing or hydrogenolysing agent,
and/or in that one or more radicals R and/or $R^2$ in a compound of the formula I are converted to one or more different radicals R and/or $R^2$ and/or a base or acid of the formula I is converted to one of its salts.

Above and below, unless expressly indicated otherwise, the radicals or parameters R, $R^1$ to $R^{16}$, A, Ar, $Het^1$, $Het^2$, Hal, k, m, n, p, t, and E are as defined in formula I.

If a compound of the formula I contains several radicals with the same designation (for example A, alkenyl, alkynyl, Ar, $R^6$, $R^7$ or $Het^2$), these can each be identical to or different from one another.

In the above formulae, A has 1–6, preferably 1, 2, 3 or 4 C atoms. A is preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, prop-1-enyl, prop-2-enyl or but-1-enyl, or else pent-1-enyl or hex-1-enyl. Alkynyl is preferably ethynyl, prop-1-ynyl or prop-2-ynyl, or else but-1-ynyl, pent-1-ynyl or hex-1-ynyl. If several radicals A, alkenyl or alkynyl are present in a compound of the formula I, they can be identical to or different from one another.

Hal is preferably F, Cl or Br, or else I.

R is a radical derived from 3H-imidazo[4,5-c]pyridine ("3H-IP") or, more precisely, 2-$R^3$-4-oxo-5-$R^4$-4,5-dihydro-3H-imidazo[4,5-c]pyridin-3-yl.

Ar is preferably unsubstituted or further, as indicated, monosubstituted phenyl; in detail preferably phenyl, o-, m- or p-tolyl, o-, m- or p-ethylphenyl, o-, m- or p-trifluoromethylphenyl, o-, m- or p-methoxyphenyl, o-, m- or p-ethoxyphenyl, o-, m- or P-difluoromethoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-carbamoylphenyl, o-, m- or p-(N-methylcarbamoyl)phenyl, o-, m- or p-(N,N-dimethylcarbamoyl)phenyl, o-, m- or p-hydroxymethylphenyl, o-, m- or P-methoxymethylphenyl, o-, m- or p-cyanophenyl, o-, m- or p-nitrophenyl, o-, m- or p-aminophenyl, o-, m- or p-methylaminophenyl, o-, m- or p-dimethylaminophenyl, o-, m- or p-trifluoroacetamidophenyl, o-, m- or p-methoxycarbonylaminophenyl, o-, m- or p-ethoxycarbonylaminophenyl, o-, m- or p-methylsulfonamidophenyl, o-, m- or p-trifluoromethylsulfonamidophenyl, o-, m- or p-fluorophenyl, o-, m- or p-chlorophenyl, o-, m- or p-bromophenyl, o-, m- or p-(1H-tetrazol-5-yl)phenyl, also preferably 2,3-, 2,4-, 2,5-, 2,6-, 3,4- or 3,5-dimethylphenyl, 2,3-, 2,4-, 2,5-, 2,6-, 3,4- or 3,5-dimethoxyphenyl.

$Het^1$ is preferably tetrahydro-2- or -3-furyl, tetrahydro-2- or -3-thienyl, 1-, 2-, 3- or 3-pyrrolidinyl, 2-, 3-, 4- or 5-oxazolidinyl, 2-, 3-, 4- or 5-thiazolidinyl, 1-, 2-, 3-, 4- or 5-imidazolidinyl, 2-, 3- or 4-tetrahydropyranyl, 2-, 3- or 4-tetrahydrothiopyranyl, 1-, 2-, 3- or 4-piperidinyl, 2-, 3- or 4-morpholinyl, 1-, 2- or 3-piperazinyl, 1-methyl-2- or -3-pyrrolidinyl, 1-methyl-2-, -3- or -4-piperidinyl, 4-methyl-2- or -3-morpholinyl, 1-methyl-2-, -3- or -4-piperazinyl, 1-phenyl-2- or -3-pyrrolidinyl, 1-phenyl-2-, -3- or -4-piperidinyl, 4-phenyl-2- or -3-morpholinyl, 1-phenyl-2-, -3- or 4-piperazinyl, 2-oxo-3-, -4- or -5-oxazolidinyl, 2-oxo-3-, -4- or -5-thiazolidinyl, 2-oxo-1-, -3-, -4- or -5-imidazolidinyl, 2,4-dioxo-1-, -3- or -5-imidazolidinyl, 2-oxo-3-phenyl-4- or -5-oxazolidinyl, 2-oxo-3-o-, -m- or -p-tolyl-4- or -5-oxazolidinyl, 2-hydroxyimino-3-, -4- or -5-oxazolidinyl, 2-methoxyimino-3-, -4- or -5-oxazolidinyl, 2-hydroxyimino-4-oxo-3- or -5-oxazolidinyl, 2-methoxyimino-4-oxo-3- or -5-oxazolidinyl.

$Het^2$ is preferably furan-2- or -3-yl, thien-2- or -3-yl, pyrrol-1-, -2- or -3-yl, imidazol-1-, -2-, -4- or -5-yl, pyrazol-1-, -3-, -4- or -5-yl, oxazol-2-, -4- or -5-yl, isoxazol-3-, -4- or -5-yl, thiazol-2-, -4- or -5-yl, isothiazol-3-, -4- or -5-yl, pyridin-2-, -3- or -4-yl or pyrimidin-2-, -4-, -5- or -6-yl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -4-yl, 1,2,3-thiadiazol-4- or -5-yl, pyridazin-3- or -4-yl, pyrazinyl, benzofuran-2-, -3-, -4-, -5-, -6- or -7-yl, benzothien-2-, -3-, -4-, -5-, -6- or -7-yl, indol-1-, -2-, -3-, -4-, -5-, -6- or -7-yl, isoindol-1-, -2-, -3-, -4-, -5-, -6- or -7-yl, benzimidazol-1-, -2-, -4- or -5-yl, benzopyrazol-1-, -3-, -4-, -5-, -6- or -7-yl, benzoxazol-2-, -4, -5-, -6- or -7-yl, benzisoxazol-3-, -4-, -5-, -6- or -7-yl, benzothiazol-2-, -4-, -5-, -6- or -7-yl, benzisothiazol-2-, -4-, -5-, -6- or -7-yl, benz-2,1,3-oxadiazol-4-, -5-, -6- or -7-yl, quinolin-2-, -3-, -4-, -5-, -6-, -7- or -8-yl, isoquinolin-1-, -3-, -4-, -5-, -6-, -7- or -8-yl, cinnolin-3-, -4-, -5-, -6-, -7- or -8-yl, quinazolin-2-, -4-, -5-, -6-, -7- or -8-yl, 1H-imidazo[4,5-b]pyridin-1-, -2-, -5-, -6- or -7-yl, 3H-imidazo[4,5-b]pyridin-2-, -3-, -5-, -6- or -7-yl, 1H-imidazo[4,5-c]pyridin-1-, -2-, -4-, -6- or -7-yl or 3H-imidazo[4,5-c]pyridin-2-, -3-, -4-, -6- or -7-yl.

The term "$Het^2$" also includes the homologous radicals in which the heteroaromatic ring is substituted by one or more, preferably 1 or 2 groups A, preferably methyl and/or ethyl groups, for example 3-, 4- or 5-methylfuran-2-yl, 2-, 4- or 5-methylfuran-3-yl, 2,4-dimethylfuran-3-yl, 3-, 4- or 5-methylthien-2-yl, 3-methyl-5-tert-butylthien-2-yl, 2-, 4- or 5-methylthien-3-yl, 2- or 3-methylpyrrol-1-yl, 1-, 3-, 4- or 5-methylpyrrol-2-yl, 3,5-dimethyl-4-ethylpyrrol-2-yl, 2-, 4- or 5-methylimidazol-1-yl, 4-methylpyrazol-5-yl, 4- or 5-methylisoxazol-3-yl, 3- or 5-methylisoxazol-4-yl, 3- or 4-methylisoxazol-5-yl, 3,4-dimethylisoxazol-5-yl, 4- or 5-methylthiazol-2-yl, 4- or 5-ethylthiazol-2-yl, 2- or 5-methylthiazol-4-yl, 2- or 4-methylthiazol-5-yl, 2,4-dimethylthiazol-5-yl, 3-, 4-, 5- or 6-methylpyridin-2-yl, 2-, 4-, 5- or 6-methylpyridin-3-yl, 2- or 3-methylpyridin-4-yl, 4-methylpyrimidin-2-yl, 4,5-dimethylpyrimidin-2-yl, 2-, 5- or 6-methylpyrimidin-4-yl, 2,6-dimethylpyrimidin-4-yl, 3-, 4-, 5-, 6- or 7-methylbenzofuran-2-yl, 2-ethylbenzofuran-3-yl, 3-, 4-, 5-, 6- or 7-methylbenzothien-2-yl, 3-ethylbenzothien-2-yl, 1-, 2-, 4-, 5-, 6- or 7-methylindol-3-yl, 1-methylbenzimidazol-5- or -6-yl or 1-ethylbenzimidazol-5- or -6-yl.

The groups —$C_kH_{2k}$—, —$C_nH_{2n}$—, —$C_pH_{2p}$— and —$C_tH_{2t}$— are preferably straight-chain and are thus preferably —$(CH_2)_n$—, —$(CH_2)_k$—, —$(CH_2)_p$— and —$(CH_2)_t$—, in particular —$CH_2$—, also —$CH_2CH_2$—, —$(CH_2)_3$—, —$(CH_2)_4$—, —$(CH_2)_5$— or —$(CH_2)_6$—, but also, for example, —$CH(CH_3)$—, —$CH_2$—$CH(CH_3)$— or —$C(CH_3)_2$—. The parameter k can preferably also be 0, so that the group —$C_kH_{2k}$— is absent.

The radical $R^1$ is preferably F.

The radical $R^3$ is preferably straight-chain and is preferably A, in particular ethyl, propyl or butyl, also methyl, pentyl or hexyl, and also cycloalkyl having 3–7 C atoms, in particular cyclopropyl, also cyclobutyl, cyclopentyl, cyclohexyl, cycloheptyl, furthermore in particular alkenyl preferably having 3–6 C atoms, in particular allyl or 1-propenyl, also 1-butenyl, 1-pentenyl or 1-hexenyl; alkynyl preferably having 3–6 C atoms, in particular propargyl or 1-propynyl, also 1-butynyl, 1-pentynyl or 1-hexynyl; cycloalkylalkyl preferably having 4–8 C atoms, in particular cyclopropylmethyl, 1- or 2-cyclopropylethyl, also cyclobutylmethyl, cyclopentylmethyl, cyclohexylmethyl; alkoxy preferably having 1–4 C atoms, such as methoxy, ethoxy, propoxy, butoxy, isobutoxy; alkoxyalkyl preferably having 2–5 C atoms, such as methoxymethyl, ethoxymethyl, propoxymethyl, 2-methoxyethyl, 3-methoxypropyl, 2-ethoxyethyl; alkylthio preferably having 1–4 C atoms such as methylthio, ethylthio, propylthio, butylthio, isobutylthio; alkylthioalkyl preferably having 2–5 C atoms such as methylthiomethyl, ethylthiomethyl, propylthiomethyl, 2-methylthioethyl, 3-methylthiopropyl and 2-ethylthioethyl.

The radical $R^4$ is preferably H; $R^8$, in particular $CH_3$, $CF_3$, $C_2H_5$, $C_2F_5$, $CH_2CF_3$, $C_3H_7$, $CH_2CH_2CF_3$, $C_4H_9$; $Ar-C_2-C_6$-alkenyl, e.g. cinnamyl; $Ar-C_2-C_6$-alkenyl substituted in the "alkenyl" moiety by COOA, e.g. 3-ethoxycarbonyl-2-phenyl-2-propene-1-yl; —$C_nH_{2n}$—$R^9$ (in detail preferably —$CH_2$—$R^9$), in particular —$C_nH_{2n}$-$C_3$-$C_8$-cycloalkyl (such as cyclopropylmethyl), cyclobutylmethyl, cyclopentylmethyl, cyclohexylmethyl, —$C_nH_{2n}$—CN (such as cyanomethyl, 2-cyanoethyl, 3-cyanopropyl), —$C_nH_{2n}$—COOA (such as methoxycarbonylmethyl, ethoxycarbonylmethyl, 2-methoxycarbonylethyl, 2-ethoxycarbonylethyl), —$C_nH_{2n}$—COOH (such as carboxymethyl, 2-carboxyethyl, 3-carboxypropyl), —$C_nH_{2n}$—Ar (such as benzyl, 1- or 2-phenylethyl, 1-, 2- or 3-phenylpropyl, 1-, 2-, 3- or 4-phenylbutyl, o-, m- or p-fluorobenzyl, (preferably) o-, m- or p-chlorobenzyl, o-, m- or p-bromobenzyl, o-, m- or p-methylbenzyl, o-, m- or p-trifluoromethylbenzyl, o-, m- or p-methoxycarbonylbenzyl, o-, m- or p-ethoxycarbonylbenzyl, o-, m- or p-cyanobenzyl, o-, m- or p-carboxybenzyl, o-, m- or p-nitrobenzyl, o-, m- or p-aminobenzyl, o-, m- or p-trifluoroacetamidobenzyl, o-, m- or p-trifluoromethylsulfonamidobenzyl, o-, m- or p-(1H-tetrazol-5-yl)benzyl, 2-chloro-6-nitrobenzyl); —$C_nH_{2n}$—$Het^1$ (preferably —$CH_2$—$Het^1$ such as —$CH_2$-(2-oxo-3-Ar-oxazolidin-5-yl), e.g. 2-oxo-3-m-tolyl-oxazolidin-5-ylmethyl); —$C_nH_{2n}$—$Het^2$ (preferably —$CH_2$—$Het^2$ such as 2- or 3-furylmethyl, 2- or 3-thienylmethyl, 5-isoxazolylmethyl, 5-methyl-3-isoxazolylmethyl, 2-, 3- or 4-pyridylmethyl, pyrazinylmethyl, 2-, 4-, 5- or 6-pyrimidinylmethyl, 3- or 4-pyridazinylmethyl, 2-, 3-, 4-, 5-, 6- or 7-benzofurylmethyl, 2-, 3-, 4-, 5-, 6- or 7-benzothienylmethyl, 2-, 3-, 4-, 5-, 6- or 7-indolylmethyl); —$C_nH_{2n}$-(1H-tetrazol-5-yl) (such as 1H-tetrazol-5-ylmethyl), 2-(1H-tetrazol-5-yl)ethyl, 3-(1H-tetrazol-5-yl)propyl; —$C_nH_{2n}$—$CONR^6R^7$ (wherein n is preferably 1 or 2, $R^6$ is preferably B or A and $R^7$ is preferably H, A, Ar, $ArC_nH_{2n}$ or $Het^2$, such as carbamoylmethyl, 2-carbamoylethyl, N-methylcarbamoylmethyl, 2-N-methylcarbamoylethyl, N-ethylcarbamoylmethyl, 2-N-ethylcarbamoylethyl, N-propylcarbamoylmethyl, 2-N-propylcarbamoylethyl, N-isopropylcarbamoylmethyl, N-butylcarbamoylmethyl, 2-N-butylcarbamoylethyl, N-isobutylcarbamoylmethyl, N-sec-butylcarbamoylmethyl, N-tert-butylcarbamoylmethyl, N,N-dimethylcarbamoylmethyl, 2-N,N-dimethylcarbamoylethyl, N-methyl-N-ethylcarbamoylmethyl, N,N-diethylcarbamoylmethyl, N,N-dipropylcarbamoyl-methyl, N,N-diisopropylcarbamoylmethyl, N,N-dibutylcarbamoylmethyl; also e.g. pyrrolidinocarbonylmethyl, piperidinocarbonylmethyl, morpholinocarbonylmethyl); —$C_nH_{2n}$—CO—NHAr, e.g. N-phenylcarbamoylmethyl, 2-N-phenylcarbamoylethyl, N-o-, -m- or -p-tolylcarbamoylmethyl, N-o-, m- or -p-trifluoromethylphenylcarbamoylmethyl, N-o-, -m- or -p-carboxyphenylcarbamoylmethyl, N-o-, -m- or -p-ethoxycarbonylphenylcarbamoylmethyl, N-o-, -m- or p-fluorophenylcarbamoylmethyl, N-o-, -m- or -p-chlorophenylcarbamoylmethyl, N-(2,3-, N-(2,4-, N-(2,5-, -N-(2,6-, N-(3,4- or N-(3,5-dimethylphenyl)carbamoylmethyl, 2-N-(2,3-, 2-N-(2,4-, 2-N-(2,5-, 2-N-(2, 6-, 2-N-(3,4- or 2-N-(3,5-dimethylphenyl)carbamoylethyl; —$C_nH_{2n}$—CO—NH—$Het^2$, e.g. N-(2-, N-(3- or N-(4-pyridyl)-carbamoylmethyl, 2-N-(2-pyridyl)-carbamoylethyl, N-(2- or N-(3-thienyl)carbamoylmethyl; —$C_nH_{2n}$—CO—NAAr, e.g. N-methyl-N-phenylcarbamoylmethyl, 2-N-methyl-N-phenylcarbamoylethyl, N-ethyl-N-phenylcarbamoylmethyl; —$C_nH_{2n}$—CO—NA($C_nH_{2n}$—Ar), e.g. N-methyl-N-benzylcarbamoylmethyl, N-methyl-N-(2-phenylethyl) carbamoylmethyl, N-methyl-N-(1,1-dimethyl-2-phenylethyl)carbamoylmethyl, 2-N-methyl-N-(1,1-dimethyl-2-phenylethyl)carbamoylethyl; —$C_nH_{2n}$—CO—N(Ar)$_2$, e.g. N,N-diphenylcarbamoylmethyl; —$C_nH_{2n}$—CO—$R^8$ (preferably —$CH_2$—CO—$R^8$ such as 2-oxopropyl, 2-oxobutyl, 3-oxobutyl, 3-methyl-2-oxobutyl, 3,3-dimethyl-2-oxobutyl, 3,3,3-trifluoro-2-oxopropyl, 3,3,4,4,4-pentafluoro-2-oxobutyl); —$C_nH_{2n}$—CO—Ar (preferably —$CH_2$—CO—Ar such as phenacyl (=2-oxo-2-phenylethyl), o-, m- or p-methylphenacyl, o-, m- or p-ethylphenacyl, o-, m- or p-trifluoromethylphenacyl, o-, m- or p-methoxyphenacyl, o-, m- or p-ethoxyphenacyl, o-, m- or p-(difluoromethoxy)-phenacyl, o-, m- or p-(trifluoromethoxy)-phenacyl, o-, m- or p-carboxyphenacyl, o-, m- or p-methoxycarbonylphenacyl, o-, m- or p-ethoxycarbonylphenacyl, o-, m- or p-cyanophenacyl, o-, m- or p-nitrophenacyl, o-, m- or p-aminophenacyl, o-, m- or p-acetamidophenacyl, o-, m- or p-trifluoroacetamidophenacyl, o-, m- or p-methylsulfonamidophenacyl, o-, m- or p-trifluoromethylsulfonamidophenacyl, o-, m- or p-(1B-tetrazol-5-yl)phenacyl); —$C_nH_{2n}$—CO—$Het^2$ (preferably —$CH_2$—CO—$Het^2$ such as 2-furoylmethyl, 2-thenoylmethyl, picolinoylmethyl, nicotinoylmethyl, isonicotinoylmethyl, pyrazinecarbonylmethyl, 2-, 4-, 5- or 6-pyrimidinecarbonylmethyl, 3- or 4-pyridazinecarbonylmethyl, benzofuran-2-, -3-, -4-, -5-, -6- or -7-carbonylmethyl, benzothiophene-2-, -3-, -4-, -5-, -6- or -7-carbonylmethyl, indole-2-, -3-, -4-, -5-, -6- or -7-carbonylmethyl); —$C_nH_{2n}$—CO—$CH_2$—$NO_2$, e.g. 3-nitro-2-oxopropyl, 4-nitro-3-oxopropyl; —$(CH_2)_x$—CO—$C_nH_{2n}$—NH—COOA, e.g. 4-BOC-amino-2-oxobutyl, 5-BOC-amino-2-oxopentyl, 6-BOC-amino-2-oxohexyl; —$C_nH_{2n}$—CO—$C_nH_{2n}$—$NH_2$, e.g. 3-amino-2-oxopropyl, 4-amino-2-oxobutyl, 5-amino-2-oxopentyl, 6-amino-2-oxohexyl, 4-amino-3-oxobutyl; —$C_nH_{2n}$—CO—NH—$SO_2Ar$, e.g. N-phenylsulfonylcarbamoylmethyl; —$C_nH_{2n}$—C(=$NR^{12}$)—A (preferably —$CH_2$—C(=$NR^{12}$)—A such as —$CH_2$(=NOH)—$CH_3$, —$CH_2$—C(=$NOCH_3$)—C($CH_3$)$_3$; —$C_nH_{2n}$—S—A, e.g. methylthiomethyl; —$C_nH_{2n}$—SO—A, e.g. methylsulfinylmethyl; —$C_nH_{2n}$—$SO_2$—A, e.g. methylsulfonylmethyl; —$C_nH_{2n}$—S—Ar, e.g. phenylthiomethyl; —$C_nH_{2n}$—SO—Ar, e.g. phenylsulfinylmethyl; —$C_nH_{2n}$—$SO_2$—Ar, e.g. phenylsulfonylmethyl; —$C_nH_{2n}$—S—$Het^2$, (2thienyl)thiomethyl; —$C_nH_{2n}$—SO—$Het^2$, e.g. (2-pyridyl)sulfinylmethyl; —$C_nH_{2n-SO2}$—$Het^2$, e.g. (2-, (3- or (4-pyridyl)sulfonylmethyl; —CH(COOA)—Ar, e.g. α-methoxycarbonylbenzyl, α-ethoxycarbonylbenzyl, α-isopropoxycarbonylbenzyl; —CH(CON(A)$_2$)—Ar, e.g. α-(N,N-dimethylcarbamoyl)benzyl.

The radical $R^5$ is preferably A, in particular methyl, ethyl, propyl, butyl, pentyl, 3-methylbutyl, 2,2-dimethylpropyl, hexyl or 4-methylpentyl; OA, in particular ethoxy, propoxy, methoxy, isopropoxy, butoxy, isobutoxy, tert-butoxy, 3-methylbutoxy; cycloalkyl, in particular cyclopropyl; cycloalkylalkyl, in particular cyclopropylmethyl, 2-cyclopropylethyl, cyclopentylmethyl, 2-cyclopentylethyl, cyclohexylmethyl, 2-cyclohexylethyl; Ar-alkyl, in particular benzyl or 2-phenylethyl; Ar-oxyalkyl, in particular phenoxymethyl; Ar-alkoxy, in particular benzyloxy, 2-phenylethoxy.

The radicals $R^6$ and $R^7$ are preferably H or A, $R^6$ is additionally preferably Ar, Ar—$C_nH_{2n}$ or $Het^2$.

Further preferred groups —$NR^6R^7$ are those in which $R^6$ and $R^7$ together are an alkylene chain having 2–5 C atoms, which can be substituted as indicated and/or interrupted by O or by —$NR^{16}$—. Particularly preferred groups —$NR^6R^7$ of this type are, for example, aziridino, pyrrolidino, piperidino, morpholino, piperazino, 2-oxopyrrolidino, 2-alkoxycarbonylpyrrolidino (wherein the alkoxy group contains 1–4 C atoms), such as 2-methoxycarbonylpyrrolidino or -ethoxycarbonylpyrrolidino, 2- or 3-alkanoylaminopyrrolidino such as 2- or 3-acetamidopyrrolidino, 2-, 3- or in particular 4-oxopiperidino, 2-, 3- or in particular 4-Ar-piperidino such as 2-, 3- or 4-phenylpiperidino, 4-o-, 4-m- or 4-p-4ethoxyphenylpiperidino, 4-o-, 4-m- or 4-p-nitrophenylpiperidino, 4-o-, 4-m- pr 4-p-chlorophenylpiperidino, 3-hydroxymethyl-4-p-chlorophenylpiperidino, 2-, 3- or 4-(2-thienyl)piperidino, 2-, 3- or 4-N,N-dimethylcarbamoylpiperidino, 2-, 3- or 4-N,N-diethylcarbamoylpiperidino, 2-, 3- or 4-benzoylpiperidino, 2-, 3- or 4-p-m-methoxybenzoylpiperidino, 4-methylpiperazino, 4-phenylpiperazino, 4-o-, 4-m- or 4-p-methoxyphenylpiperazino, 4-o-, 4-m- or 4-p-nitrophenylpiperazino, 4-o-, 4-m- or 4-p-chlorophenylpiperazino, 4-(2-pyrimidinyl)piperazino, 4-methoxycarbonylpiperazino, 4-ethoxycarbonylpiperazino, 4-BOC-piperazino, 4-phenylsulfonylpiperazino, 4-p-tolylsulfonylpiperazino, 4-o-, 4-m- or 4-p-fluorophenylsulfonylpiperazino.

The radical $R^8$ preferably contains 1, 2 or 3 C atoms and is preferably methyl, ethyl, trifluoromethyl, pentafluoroethyl, 2,2,2-trifluoroethyl or 3,3,3-trifluoropropyl.

$R^9$ is preferably At, —COOA, —COOH or —CO—$NR^6R^7$, also preferably —CO—$R^8$, —CO—Ar, —CO—$R^{14}$ or —C(=$NR^{12}$)—A.

$R^{10}$ is preferably COOH or COOA.

$R^{11}$ is preferably Ar, in particular phenyl.

$R^{12}$ is preferably OH or $OR^{16}$, in particular OA.

$R^{13}$ is preferably A.

$R^{14}$ is preferably —$C_nH_{2n}$—$NO_2$ or —$C_nH_{2n}$—$NR^6R^7$, in particular —$C_nH_{2n}$—$NH_2$.

$R^{15}$ is preferably H, also A having 1–4 C atoms.

$R^{16}$ is preferably H or A.

The parameter k is preferably 0 or 1. The parameter m is preferably 0 or 2. The parameter n is preferably 1, also preferably 2, 3 or 4. The parameter p is preferably 1 or 2.

The compounds of the formula I can possess one or more chiral centres and can therefore exist in different forms (optically active or optically inactive). Formula I includes all these forms.

Accordingly the invention relates especially to those compounds of the formula I in which at least one of said radicals has one of the preferred meanings indicated above.

Some preferred groups of compounds can be expressed by the following partial formulae Ia to Ie, which correspond to formula I and wherein the radicals not described more precisely are as defined in formula I, except that:

in Ia $R^1$ is F, Cl or Br;

in Ib $R^1$ is F;

in Ic $R^1$ is F, Cl or Br and $R^5$ is —$C_rH_{2r}$-($C_3$–$C_8$-cycloalkyl) or —$C_rH_{2r}$—Ar;

in Id $R^1$ is F and $R^5$ is —$C_rH_{2r}$-($C_3$–$C_8$-cycloalkyl) or —$C_rH_{2r}$—Ar;

in Ie $R^1$ is F and $R^5$ is —$CH_2CH_2$-cyclopentyl or —$CH_2CH_2C_6H_5$.

Among these, those compounds are preferred wherein $R^3$ is A or alkenyl each having 3–6 C atoms or cyclopropyl.

Other preferred groups of compounds have formula I and the other formulae given above, except that the radical $R^4$ is defined as follows:

(a) alkenyl-Ar having 2–6 C atoms in the "alkenyl" moiety, (b) —$C_nH_{2n}$—$R^9$, (c) —$C_nH_{2n}$—Ar, (d) —$C_nH_{2n}$—CO—$NR^6R^7$, (e) —$CH_2$—CO—$NR^6R^7$, wherein $R^6$ and $R^7$ are each H, A or phenyl, (f) —$CH_2$—CO—$NR^6R^7$, wherein $R^6$ and $R^7$ together are an alkylene chain having 2–5 C atoms which can be monosubstituted or polysubstituted by carbonyl oxygen, Ar, $Het^2$, —CO—Ar, —COOA, —CO—N(A)$_2$, —$CH_2OH$, —$SO_2$—Ar and/or —NH—CO—A and/or interrupted by O or by —$NR^{16}$—, (g) —$CH_2$—CO—$NR^6R^7$, wherein —$NR^6R^7$ is pyrrolidino, piperidino or morpholino, (h) H, (i) A, (j) —$CH_2$Ar, (k) —$CH_2COOH$, (l) —$CH_2COOA$, (m) —$CH_2$—CO—Ar, (n) —$CH_2$-thienyl, (o) cinnamyl, (p) —CH(COOA)—Ar, (q) —$CH_2$—S(O)$_m$—Ar, (r) —$CH_2$—S—Ar, (s) —$CH_2$—$SO_2$Ar.

The compounds of the formula I and also the starting materials for their preparation are moreover prepared analogously by methods known per se, such as those described in the literature (for example in the standard works like Houben-Weyl, Methoden der organischen Chemie (Methods of Organic Chemistry), Georg-Thieme-Verlag, Stuttgart, but especially in European Patent Application A2-0 430 709, and in U.S. Pat. No. 4,880,804), under conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of the formula I.

(a) Compounds of the formula I can preferably be obtained by N-acylation of compounds which correspond to the formula I, but contain an —$SO_2NH_2$ group in place of a radical $R^2$. Suitable acylating agents are e.g. compounds of the formula E—CO—$R^5$, wherein E is a leaving group, preferably Cl, Br, I or a reactive functionally modified OH group such as alkylsulfonyloxy having 1–6 C atoms (preferably methylsulfonyloxy) or arylsulfonyloxy having 6–10 C atoms (preferably phenyl- or p-tolylsulfonyloxy). Examples of such compounds are methyl and ethyl chloroformates; acetyl chloride, cyclopropanecarbonyl chloride, benzoyl chloride, phenylacetyl chloride, 3-phenylpropionyl chloride, cyclopentylacetyl chloride, 3-cyclopentylpropionyl chloride.

The reaction can be carried out in the presence of one or more bases, preferably of a tertiary amine, e.g. triethylamine, pyridine, 4-dimethylaminopyridine, expediently at temperatures about 0°–100°. An excess of the amine can also be used as a solvent.

(b) It is also possible to free a compound of the formula I from one of its functional derivatives by solvolysis (for example hydrolysis) or hydrogenolysis.

Thus carboxylic acids of the formula I which contain (at least) one COOH group can be obtained by the saponification of corresponding alkyl esters, for example with NaOH or KOH in aqueous solution, with or without the addition of an inert organic solvent such as methanol, ethanol, THF or dioxane, at temperatures of about 0°–100°, or by the hydrogenolysis of corresponding benzyl esters, for example on Pd-on-charcoal at pressures of about 1–200 bar and at temperatures of about 0°–100°, in one of the inert solvents indicated.

The starting materials, especially those of the formula E—CO—$R^5$, are known extensively. If they are not known, they can be prepared by known methods analogously to known substances.

It is also possible to convert one compound of the formula I to another compound of the formula I by converting one or more of the radicals R and/or $R^2$ to other radicals R and/or $R^2$, for example by reacting a compound of the formula I ($R^4$=H) with a compound of the formula E—$R^4$ (wherein $R^4$ is different from H) or by reducing nitro groups to amino groups. (for example by hydrogenation on Raney nickel or Pd-on-charcoal in an inert solvent such as methanol or ethanol), and/or functionally modifying free amino and/or hydroxyl groups, and/or freeing functionally modified amino and/or hydroxyl groups by solvolysis or hydrogenolysis, and/or hydrolysing nitrile groups to COOH groups, and/or oxidizing thioether groups to SO or $SO_2$ groups, for example with $H_2O_2$ or a peracid such as 3-chloroperbenzoic acid and/or converting compounds of the formula I which contain a carbonyl group to compounds of the formula I which contain a —C(=$NR^{12}$) group, e.g. by reaction with a compound of the formula $H_2N$—$R^{12}$, such as ammonia, hydroxylamine, O-alkyl-, O-alkenyl-, O-alkynyl- or O-arylhydroxylamines, cyanamide or primary amines of the formula $H_{2N}$—$R^{13}$, esterifying or amidating a carboxylic acid group, e.g. by reaction with an alcohol of the formula A—OH or with an amine of the formula $HNR^6R^7$ or of the formula $H_{2N}$—$CHR^{15}$—COOA.

In the alkylation of compounds of the formula I ($R^4$=H) by reaction with compounds of the formula E—$R^4$, the reaction is preferably carried out in an inert solvent, e.g. an acid amide such as DMF, N-methylpyrrolidone, 1,3-dimethyl-2-oxohexahydropyrimidine or hexamethylphosphoramide, an alcohol such as methanol or tert-butanol, an ether such as THF or a halogenated hydrocarbon such as dichloromethane or mixtures thereof and/or in the presence of an alkali metal alkoxide such as sodium methoxide or potassium tert-butoxide, of an alkali metal hydride such as sodium hydride or potassium hydride, of an alkali metal carbonate such as sodium carbonate or potassium carbonate, of an alkali metal bicarbonate such as sodium bicarbonate or potassium bicarbonate or of a tertiary amine such as triethylamine or ethyldiisopropylamine at temperatures about –30°–200°, preferably 10°–60° C.

Furthermore, free amino groups can be acylated in conventional manner with an acid chloride or anhydride, or alkylated with an unsubstituted or substituted alkyl halide, conveniently in an inert solvent such as methylene chloride or THF, and/or in the presence of a base such as triethylamine or pyridine, at temperatures of about –60°–+30°.

If desired, a functionally modified amino and/or hydroxyl group in a compound of the formula I can be freed by solvolysis or hydrogenolysis using conventional methods. Thus, for example, a compound of the formula I containing an $NHCOR^{11}$ or COOA group can be converted to the corresponding compound of the formula I containing an $NH_2$ or HOOC group instead. COOA groups can be saponified for example with NaOH or KOH in water, water/THF or water/dioxane, at temperatures of between 0° and 100°.

In the amidation of carboxylic acid groups, the reaction is expediently carried out according to customary methods of peptide synthesis, as are described e.g. in Houben-Weyl, l.c., Volume 15/II, pages 1–806 (1974). The reaction is preferably carried out in the presence of a dehydrating agent, e.g. of a carbodiimide such as N,N'-dicyclohexylcarbodiimide ("DCCI"), 1,1'-carbonyldiimidazole or N-3-dimethylaminopropyl-N'-ethylcarbodiimide ("DAPECI"), also propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, e.g. a halogenated hydrocarbon such as dichloromethane, an ether such as THF or dioxane, an amide such as DMF or dimethylacetamide, a nitrile such as acetonitrile, at temperatures between about –10°–40°, preferably between 0°–30°.

In place of the carboxylic acids, suitable reactive derivatives of these substances can also be employed in the reaction, e.g. those in which reactive groups are blocked intermediately by protective groups. The acids can be used e.g. in the form of their activated esters, which are expediently formed in situ, e.g. by addition of 1-hydroxybenzotriazole or N-hydroxysuccinimide.

A base of the formula I can be converted with an acid to the corresponding acid addition salt, for example by reaction of equivalent amounts of the base and of the acid in an inert solvent such as ethanol and subsequent evaporation. Possible acids for this reaction are especially those which yield physiologically acceptable salts. Thus it is possible to use inorganic acids, for example sulfuric acid, nitric acid, hydrohalic acids such as hydrochloric acid or hydrobromic acid, phosphoruorthophosphoric acids such as orthophosphoric acid, and sulfamic acid, as well as organic acids, especially aliphatic, alicyclic, araliphatic, aromatic or heterocyclic monobasic or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethane-sulfonic acid, ethanedisulfonic acid, 2-hydroxyethanesulfonic acid, benzenesulfonic acid, p-toluenesulfonic acid, naphthalene-monosulfonic and -disulfonic acids and laurylsulfuric acid. Salts with physiologically unacceptable acids, for example picrates, can be used for isolating and/or purifying the compounds of the formula I.

On the other hand, compounds of the formula I containing COOH or, for example, tetrazole groups can be converted with bases (for example sodium or potassium hydroxide or carbonate) to the corresponding metal salts, especially alkali metal or alkaline earth metal salts, or to the corresponding ammonium salts. The potassium salts of the tetrazole derivatives are particularly preferred.

The compounds of the formula I can have one or more chiral centres and, accordingly, be present in various enantiomeric or diastereomeric forms which can be separated in the conventional manner. Formula I encompasses all these forms.

The novel compounds of the formula I and their physiologically acceptable salts can be used for the manufacture of pharmaceutical preparations by incorporation into a suitable dosage form together with at least one excipient or adjunct and, if desired, together with one or more other active ingredients. The resulting formulations can be used as drugs in human or veterinary medicine. Possible excipients are organic or inorganic substances which are suitable for enteral (for example oral or rectal) or parenteral administration or for administration in the form of an inhalation spray, and which do not react with the novel compounds, examples being water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; special lacquered tablets and capsules with coatings or shells resistant to gastric juices are of interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant gas mixture. It is convenient here to use the active ingredient in micronised form, it being possible for one or more additional physiologically compatible solvents, for example ethanol, to be added. Inhalation solutions can be administered with the aid of conventional inhalers. The novel compounds can be lyophilised and the resulting lyophilisates used for example for the manufacture of injectable preparations. The indicated formulations can be sterilised and/or can contain adjuncts such as preservatives, stabilisers and/or wetting agents, emulsifiers, salts for influencing the osmotic pressure, buffer substances and colours and/or flavourings. If desired, they can also contain one or more other active ingredients, for example one or more vitamins, diuretics or antiphlogistics.

The substances according to the invention are normally administered analogously to other known, commercially available preparations, for example captopril or enalapril, but in particular analogously to the compounds described in U.S. Pat. No. 4,880,804, preferably in doses of about 1 mg–1 g, especially of 10–100 mg per dosage unit. The daily dose is preferably about 0.02–10 mg/kg, especially 0.1–1 mg/kg of body weight. However, the particular dose for each individual patient depends on a very wide variety of factors, for example on the efficacy of the particular compound used, age, body weight, general state of health, sex, diet, time and mode of administration, rate of excretion, drug combination and severity of the particular disease to which the therapy is applied. Oral administration is preferred.

Above and below, all temperatures are given in °C. In the following Examples, "conventional working-up" means: Water is added if necessary, the pH is adjusted to between 2 and 10 if necessary, depending on the constitution of the end product, extraction is carried out with ethyl acetate or methylene chloride and the organic phase is separated off, dried over sodium sulfate, evaporated and purified by chromatography on silica gel and/or by crystallization.

IP=imidazo[4,5-c]pyridine, IPs=imidazo[4,5-c]pyridines, Rf values on silica gel; mobile phase; ethyl acetate/methanol 9:1;

$M^+$=mass spectrum (EI)—molecular peak.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 44 32 860.5, are hereby incorporated by reference.

EXAMPLE 1

A solution of 170 mg of 3-phenylpropionyl chloride in 2 ml of pyridine is added to a solution of 539 mg of 2-butyl-3-(2'-aminosulfonyl-3-fluorobiphenyl-4-ylmethyl)-4,5-dihydro-4-oxo-5,N,N-dimethylcarbamoylmethyl-3H-1P ["A"; oily, Rf 0.23; obtainable by reaction of 2-butyl-4-oxo-4,5-dihydro-1(or 3)H-IP with 4'-bromomethyl-3-fluorobiphenyl-2-(N-tert-butyl)sulfonamide (m.p. 148°–149°) to give 2-butyl-3-(2'-N-tert-butylaminosulfonyl-3-fluorobiphenyl-4-ylmethyl)-4,5-dihydro-4-oxo-3H-IP ("B"; m.p. 259°–260°), reaction with N,N-dimethylchloroacetamide/K tert-butoxide in DMF at 20° to give 2-butyl-3-(2'-N-tert-butylaminosulfonyl-3-fluorobiphenyl-4-ylmethyl)-4,5-dihydro-4-oxo-5-N,N-dimethylcarbamoylmethyl-3H-IP (m.p. 177°–178°) and removal of the tert-butyl group using $CF_3COOH$/anisole] and 360 mg of 4-dimethylaminopyridine in 12 ml of pyridine, the fixture is stirred at 20° for 48 hours, 8 ml of methanol are added and it is worked up in the conventional manner. 2-Butyl-3-(2'-(3-phenylpropionylaminosulfonyl)-3-fluorobiphenyl-4-ylmethyl)-4,5-dihydro-4-oxo-5-N,N-dimethylcarbamoylmethyl-3H-IP is obtained, m.p. 204°–205°.

The following are obtained analogously from using
valeryl chloride
hexanoyl chloride
4-methylpentanoyl chloride
3,3-dimethylbutyryl chloride
heptanoyl chloride
5-methylhexanoyl chloride
cyclopropylcarbonyl chloride
3-cyclopentylpropionyl chloride
phenylacetyl chloride
ethyl chloroformate
butyl chloroformate
isobutyl chloroformate
tert-butyl chloroformate
isopentisopentyl chloroformate (=3-methylbutyl chloroformate)
benzyl chloroformate
phenoxyacetyl chloride
the 2-butyl-3-(2'-$R^2$-3-fluorobiphenyl-4-ylmethyl)-4,5-dihydro-4-oxo-5-N,N-dimethylcarbamoylmethyl-3H-Ips below:
-2'-valerylaminosulfonyl-
-2'-hexanoylaminosulfonyl-
-2'-(4-methylpentanoylaminosulfonyl)-, m.p. 112°–113°
-2'-(3,3-dimethylbutyrylaminosulfonyl)-
-2'-heptanoylaminosulfonyl-
-2'-(5-methylhexanoylaminosulfonyl)-
-2'-cyclopropylcarbonylaminosulfonyl- -2'-(3-cyclopentylpropionylaminosulfonyl)-, Rf 0.39
-2'-phenylacetylaminosulfonyl-
-2'-(N-ethoxycarbonylaminosulfonyl)-
-2'-(N-butoxycarbonylaminosulfonyl)-
-2'-(N-isobutoxycarbonylaminosulfonyl)-
-2'-(N-tert-butoxycarbonylaminosulfonyl)-
-2'-(N-isopentyloxycarbonylaminosulfonyl)-
-2'-(N-benzyloxycarbonylaminosulfonyl)-
-2'-phenoxyacetylaminosulfonyl-.

The 2-butyl-3-(2'-(N-tert-butylaminosulfonyl)-3-fluorobiphenyl-4-ylmethyl)-4,5-dihydro-4-oxo-5-$R^4$-3H-IPs below are obtained analogously from "B" using the corresponding halides (e.g. ethyl bromide):
-5-ethyl-
-5-propyl-
-5-butyl-
-5-methoxycarbonylmethyl-
-5-ethoxycarbonylmethyl-
-5-carbamoylmethyl-
-5-N-ethylcarbamoylmethyl-
-5-N-butylcarbamoylmethyl-
-5-N,N-diethylcarbamoylmethyl-
-5-N-phenylcarbamoylmethyl-
-5-(2-N-ethylcarbamoylethyl)-
-5-(2-N-butylcarbamoylethyl)-
-5-(2-N,N-dimethylcarbamoylethyl)-
-5-(2-N-phenylcarbamoylethyl)-
-5-(2-oxopropyl)-
-5-(3-oxobutyl)-
-5-(2-oxo-3,3-dimethylbutyl)-
-5-phenacyl-
-5-(2-methoxyphenacyl)-
-5-pyrrolidinocarbonylmethyl-
-5-piperidinocarbonylmethyl-
-5-morpholinocarbonylmethyl-
-5-benzyl-
-5-(2-methoxycarbonylbenzyl)-
-5-(2-ethoxycarbonylbenzyl)-
-5-(2-thienylmethyl)-
-5-(α-(N,N-dimethylcarbamoyl)benzyl)-
-5-(2-oxohexyl)-
-5-benzoylethyl-
-5-N-tert-butylcarbamoylmethyl-
-5-(α-isopropoxycarbonylbenzyl)-
-5-phenylthiomethyl-
-5-phenylsulfinylmethyl-
-5-N-benzylcarbamoylmethyl-
-5-N-propylcarbamoylmethyl-
-5-N-(2-methylpropyl)carbamoylmethyl-
-5-N-pentylcarbamoylmethyl-,
therefrom the 2-butyl-3-(2'-(aminosulfonyl)-3-fluorobiphenyl-4-ylmethyl)-4,5-dihydro-4-oxo-5-$R^4$-3H-IPs below:
-5-ethyl-
-5-propyl-
-5-butyl-
-5-methoxycarbonylmethyl-
-5-ethoxycarbonylmethyl-
-5-carbamoylmethyl-
-5-N-ethylcarbamoylmethyl-
-5-N-butylcarbamoylmethyl-
-5-N,N-diethylcarbamoylmethyl-
-5-N-phenylcarbamoylmethyl-
-5-(2-N-ethylcarbamoylethyl)-
-5-(2-N-butylcarbamoylethyl)-
-5-(2-N,N-dimethylcarbamoylethyl)-
-5-(2-N-phenylcarbamoylethyl)-
-5-(2-oxopropyl)-
-5-(3-oxobutyl)-
-5-(2-oxo-3,3-dimethylbutyl)-
-5-phenacyl-
-5-(2-methoxyphenacyl)-
-5-pyrrolidinocarbonylmethyl-
-5-piperidinocarbonylmethyl-
-5-morpholinocarbonylmethyl-
-5-benzyl-
-5-(2-methoxycarbonylbenzyl)-
-5-(2-ethoxycarbonylbenzyl)-
-5-(2-thienylmethyl)-
-5-(α-(N,N-dimethylcarbamoyl)benzyl)-
-5-(2-oxohexyl)-
-5-benzoylethyl-
-5-N-tert-butylcarbamoylmethyl-
-5-(α-isopropoxycarbonylbenzyl)-
-5-phenylthiomethyl-
-5-phenylsulfinylmethyl-
-5-N-benzylcarbamoylmethyl-
-5-N-propylcarbamoylmethyl-
-5-N-(2-methylpropyl)carbamoylmethyl-
-5-N-pentylcarbamoylmethyl-,
and therefrom with 3-phenylpropionyl chloride the 2-butyl-3-(2,-(3-phenylpropionylaminosulfonyl)-3-fluorobiphenyl-4-ylmethyl)-4,5-dihydro-4-oxo-5-$R^4$3H-IPs below:
-5-ethyl-
-5-propyl-
-5-butyl-
-5-methoxycarbonylmethyl-, Rf (ethyl acetate) 0.44; $M^+$ 658
-5-ethoxycarbonylmethyl-, m.p. 125°–126°
-5-carbamoylmethyl-
-5-N-ethylcarbamoylmethyl-
-5-N-butylcarbamoylmethyl-, Rf 0.55; $M^+$ 699
-5-N,N-diethylcarbamoylmethyl-, m.p. 157°–158°
-5-N-phenylcarbamoylmethyl-
-5-(2-N-ethylcarbamoylethyl)-
-5-(2-N-butylcarbamoylethyl)-
-5-(2-N,N-dimethylcarbamoylethyl)-
-5-(2-N-phenylcarbamoylethyl)-
-5-(2-oxopropyl)-, Rf 0.75; $M^+$ 642
-5-(3-oxobutyl)-
-5-(2-oxo-3,3-dimethylbutyl)-, m.p. 126°–127°
-5-phenacyl-, m.p. 144°–145°
-5-(2-methoxyphenacyl)-
-5-pyrrolidinocarbonylmethyl-
-5-piperidinocarbonylmethyl-, m.p. 204°–205°
-5-morpholinocarbonylmethyl-
-5-benzyl-, m.p. 121°–122°
-5-(2-methoxycarbonylbenzyl)-
-5-(2-ethoxycarbonylbenzyl)-
-5-(2-thienylmethyl)-
-5-(α-(N,N-dimethylcarbamoyl)benzyl)-
-5-(2-oxohexyl)-, m.p. 89°–90°
-5-benzoylethyl-, m.p. 67°–68°
-5-N-tert-butylcarbamoylmethyl-, m.p. 116°–117°
-5-(α-isopropoxycarbonylbenzyl)-
-5-phenylthiomethyl-
-5-phenylsulfinylmethyl-
-5-N-benzylcarbamoylmethyl, m.p. 128°–129°
-5-N-propylcarbamoylmethyl, m.p. 125°–126°
-5-N-(2-methylpropyl)carbamoylmethyl, m.p. 127°–128°
-5-N-pentylcarbamoylmethyl-

EXAMPLE 2

Analogously to Example 1, 2-ethyl-3-(2'-(3-phenylpropionylaminosulfonyl)-3-fluorobiphenyl-4- ylmethyl)-4,5-dihydro-4-oxo-5-N,N-dimethylcarbamoylmethyl-3H-IP, m.p. 226°–227°, is obtained from 2-ethyl-3-(2'-aminosulfonyl-3-fluorobiphenyl-4-ylmethyl)-4,5-dihydro-4-oxo-5-N,N-dimethylcarbamoylmethyl-3H-IP (obtainable via 2-ethyl-4,5-dihydro-4-oxo-1(or 3)H-IP, 2-ethyl-3-(2'-N-tert-butylaminosulfonyl-3-fluorobiphenyl-4-ylmethyl)-4,5-dihydro-4-oxo-3H-1P and 2-ethyl-3-(2'-N-tert-butylaminosulfonyl-3-fluorobiphenyl-4-ylmethyl)-4,5-dihydro-4-oxo-3H-1P and 2-ethyl-3-(2'-N-tert-butylaminosulfonyl-3-fluorobiphenyl-4-ylmethyl)-4,5-dihydro-4-oxo-5-N,N-dimethylcarbamoylmethyl-3H-IP) using 3-phenylpropionyl chloride.

The 2-ethyl-3-(2'-R$^2$-3-fluorobiphenyl-4-ylmethyl)-4,5-dihydro-4-oxo-5-N,N-dimethylcarbamoylmethyl-3H-IPs below are obtained analogously using the acid chlorides indicated in Example 1:
-2'-valerylaminosulfonyl-
-2'-hexanoylaminosulfonyl-
-2'-(4-methylpentanoylaminosulfonyl)-
-2'-(3,3-dimethylbutyrylaminosulfonyl)-
-2'-heptanoylaminosulfonyl-
-2'-(5-methylhexanoylaminosulfonyl)-
-2'-cyclopropylcarbonylaminosulfonyl-
-2'-(3-cyclopentylpropionylaminosulfonyl)-
-2'-phenylacetylaminosulfonyl-
-2'-(N-ethoxycarbonylaminosulfonyl)-
-2'-(N-butoxycarbonylaminosulfonyl)-
-2'-(N-isobutoxycarbonylaminosulfonyl)-
-2'-(N-tert-butoxycarbonylaminosulfonyl)-
-2'-(N-isopentyloxycarbonylaminosulfonyl)-
-2'-(N-benzyloxycarbonylaminosulfonyl)-
-2'-phenoxyacetylaminosulfonyl-.

EXAMPLE 3

Analogously to Example 1, 2-propyl-3-(2'-(3-phenylpropionylaminosulfonyl)-3-fluorobiphenyl-4-ylmethyl)-4,5-dihydro-4-oxo-5-N,N-dimethylcarbamoylmethyl-3HB-IP, m.p. 202°–203°, is obtained from 2-propyl-3-(2'-aminosulfonyl-3-fluorobiphenyl-4-ylmethyl)-4,5-dihydro-4-oxo-5-N,N-dimethylcarbamoylmethyl-3H-IP (obtainable via 2-propyl-4,5-dihydro-4-oxo-1(or 3)H-IP, 2-propyl-3-(2'-N-tert-butylaminosulfonyl-3-fluorobiphenyl-4-ylmethyl)-4,5-dihydro-4-oxo-3H-IP and 2-propyl-3-(2'-N-tert-butylaminosulfonyl-3-fluorobiphenyl-4-ylmethyl)-4,5-dihydro-4-oxo-5-N,N-dimethylcarbamoylmethyl-3H-IP) using 3-phenylpropionyl chloride.

The 2-propyl-3-(2'-R$^2$-3-fluorobiphenyl-4-ylmethyl)-4,5-dihydro-4-oxo-5-N,N-dimethylcarbamoylmethyl-3H-IPs below are obtained analogously using the acid chlorides indicated in Example 1:
-2'-valerylaminosulfonyl-
-2'-hexanoylaminosulfonyl-
-2'-(4-methyl-pentanoylaminosulfonyl)-
-2'-(3,3-dimethylbutyrylaminosulfonyl)-
-2'-heptanoylaminosulfonyl-
-2'-(5-methylhexanoylaminosulfonyl)-
-2'-cyclopropylcarbonylaminosulfonyl-
-2'-(3-cyclopentylpropionylaminosulfonyl)-
-2'-phenylacetylaminosulfonyl-
-2'-(N-ethoxycarbonylaminosulfonyl)-
-2'-(N-butoxycarbonylaminosulfonyl)-
-2'-(N-isobutoxycarbonylaminosulfonyl)-
-2'-(N-tert-butoxycarbonylaminosulfonyl)-
-2'-(N-isopentyloxycarbonylaminosulfonyl)-
-2'-(N-benzyloxycarbonylaminosulfonyl)-
-2'-phenoxyacetylaminosulfonyl-.

EXAMPLE 4

Analogously to Example 1, 2-butyl-3-(2'-(3-phenylpropionylaminosulfonyl)-3-fluorobiphenyl-4-ylmethyl)-4,5-dihydro-4-oxo-3H-IP is obtained from 2-butyl-3-(2'-aminosulfonyl-3-fluorobiphenyl-4-ylmethyl)-4,5-dihydro-4-oxo-3H-IP (which can be prepared from "B" by removal of the tert-butyl group using CF$_3$COOH/anisole) and 3-phenylpropionyl chloride.

2-Butyl-3-(2'-(3-cyclopentylpropionylaminosulfonyl)-3-fluorobiphenyl-4-ylmethyl)-4,5-dihydro-4-oxo-3H-IP is obtained analogously.

EXAMPLE 5

A solution of 1 g of 2-butyl-3-(2'-(3-phenylpropionylaminosulfonyl)-3-fluorobiphenyl-4-ylmethyl)-4,5-dihydro-4-oxo-5-benzyloxycarbonylmethyl-3H-IP (obtainable by reaction of "B" with benzyl chloroacetate, subsequent removal of the tert-butyl group and acylation with 3-phenylpropionyl chloride, in 25 ml of methanol is hydrogenated to completion at normal pressure and at 20° on 0.2 g of 5% Pd/C. The mixture is filtered and evaporated, and 2-butyl-3-(2'-(3-phenylpropionylaminosulfonyl)-3-fluorobiphenyl-4-ylmethyl)-4,5-dihydro-4-oxo-5-carboxymethyl-3H-IP, m.p. 131°–132°, is obtained.

EXAMPLE 6

A solution of 5.80 g of 2-butyl-3-(2'-(3-cyclopentylpropionylaminosulfonyl)-3-fluorobiphenyl-4-ylmethyl)-4,5-dihydro-4-oxo-3H-IP (see Example 4) in 35 ml of DMF is treated with stirring at 20° with 2.5 g of K tert-butoxide. After stirring for 45 min, a solution of 1.27 g of benzyl chloride in 15 ml of DMF is added dropwise. The mixture is stirred at 20° for a further 16 hours and worked up in the conventional manner, and 2-butyl-3-(2'-(3-cyclopentylpropionylaminosulfonyl)-3-fluorobiphenyl-4-ylmethyl)-4,5-dihydro-4-oxo-5-benzyl-3H-IP is obtained.

The 2-butyl-3-(2'-(3-cyclopentylpropionylaminosulfonyl)-3-fluorobiphenyl-4-ylmethyl)-4,5-dihydro-4-oxo-5-R$^3$-3H-IPs are obtained analogously:
with ethyl iodide:
-5-ethyl-
with methyl bromoacetate:
-5-methoxycarbonylmethyl-
with ethyl bromoacetate:
-5-ethoxycarbonylmethyl-
with tert-butyl bromoacetate:
-5-tert-butoxycarbonylmethyl-
with bromoacetamide:
-5-carbamoylmethyl-
with N,N-dimethylchloroacetamide:
-5-N,N-dimethylcarbamoylmethyl-, Rf 0.39
with N,N-diethylchloroacetamide:
-5-N,N-diethylcarbamoylmethyl-
with N,N-diphenylchloroacetamide:
-5-N,N-diphenylcarbamoylmethyl-
with N-phenylchloroacetamide:
-5-N-phenylcarbamoylmethyl-
with N-methyl-N-phenylchloroacetamide:
-5-N-methyl-N-phenylcarbamoylmethyl-
with bromoacetone:
-5-(2-oxopropyl)-
with 2-oxo-3,3-dimethylbutyl bromide:
-5-(2-oxo-3,3-dimethylbutyl)-
with phenacyl bromide:

-5-phenacyl-
with 2-methoxyphenacyl bromide:
-5-(2-methoxyphenacyl)-
with bromoacetic acid pyrrolidide:
-5-pyrrolidinocarbonylmethyl-
with bromoacetic acid piperidide:
-5-piperidinocarbonylmethyl-
with bromoacetic acid morpholide:
-5-morpholinocarbonylmethyl-
with ethyl 2-bromomethylbenzoate:
-5-(2-ethoxycarbonylbenzyl)-
with 2-chlorobenzyl bromide:
-5-(2-chlorobenzyl)-
with 2-thienylmethyl chloride:
-5-(2-thienylmethyl)-
with methyl α-bromophenylacetate:
-5-α-methoxycarbonylbenzyl)-
with isopropyl α-bromophenylacetate:
-5-(α-isopropoxycarbonylbenzyl)-
with α-bromo-(N,N-dimethyl)phenylacetamide:
-5-(α-N,N-dimethylcarbamoyl)-benzyl)-
with phenylthiomethyl chloride:
-5-phenylthiomethyl-
with phenylsulfonylmethyl chloride:
-5-phenylsulfonylmethyl-.

EXAMPLE 7

A mixture of 1 g of 2-butyl-3-(2'-(3-phenylpropionylaminosulfonyl)-3-fluorobiphenyl-4-ylmethyl)-4,5-dihydro-4-oxo-5-ethoxycarbonylmethyl-3H-IP, 12 ml of aqueous 2N NaOH solution and 48 ml of methanol is stirred at 20° for 48 hours and then evaporated. The mixture is worked up with aqueous hydrochloric acid/dichloromethane in the conventional manner and 2-butyl-3-(2'-(3-phenylpropionylaminosulfonyl)-3-fluorobiphenyl-4-ylmethyl)-4,5-dihydro-4-oxo-3H-IP-5-acetic acid is obtained.

EXAMPLE 8

Analogously to Example 3, 2-propyl-3-(2'-N-tert-butylaminosulfonyl-3-fluorobiphenyl-4-ylmethyl)-4,5-dihydro-4-oxo-3H-IP ("C") is obtained by reaction of 2-propyl-4,5-dihydro-4-oxo-1(or 3)H-IP with 4'-bromomethyl-3-fluorobiphenyl-2-(N-tert-butyl) sulfonamide. By reaction of "C" with the appropriate halides, the 2-propyl-3-(2'-(N-tert-butylaminosulfonyl)-3-fluorobiphenyl-4-ylmethyl)-4,5-dihydro-4-oxo-5-$R^4$-3H-IP compounds below are obtained in which $R^4$ is
-N-tert-butylcarbamoylmethyl-
-piperidinocarbonylmethyl-
-N-butylcarbamoylmethyl-
-N-propylcarbamoylmethyl-
-N-pentylcarbamoylmethyl-
-N-(2-methylpropyl)carbamoylmethyl-
-N-(3-methylbutyl)carbamoylmethyl-
-N-(4-methylpentyl)carbamoylmethyl-,
therefrom the 2-propyl-3-(2'-aminosulfonyl-3-fluorobiphenyl-4-ylmethyl)-4,5-dihydro-4-oxo-5-$R^4$-3H-IP compounds below, in which $R^4$ is:
-N-tert-butylcarbamoylmethyl-
-piperidinocarbonylmethyl -
-N-butylcarbamoylmethyl-
-N-propylcarbamoylmethyl-
-N-pentylcarbamoylmethyl-
-N-(2-methylpropyl)carbamoylmethyl-
-N-(3-methylbutyl)carbamoylmethyl-
-N-(4-methylpentyl)carbamoylmethyl-,
and therefrom with 3-phenylpropionyl chloride the 2-propyl-3-(2'-(3-phenylpropionylaminosulfonyl)-3-fluorobiphenyl-4-ylmethyl)-4,5-dihydro-4-oxo-5-$R^4$-3H-IP compounds below:
-5-N-tert-butylcarbamoylmethyl-, m.p. 109°–110°
-5-piperidinocarbonylmethyl-, m.p. 206°–207°
-5-N-butylcarbamoylmethyl-, m.p. 121°–122°
-5-N-propylcarbamoylmethyl-, m.p. 167°–168°
-5-N-pentylcarbamoylmethyl-, m.p. 131°–132°
-5-N-(2-methylpropyl)carbamoylmethyl-, m.p. 124°–125°
-5-N-(3-methylbutyl)carbamoylmethyl-, m.p. 107°–108°
-5-N-(4-methylpentyl)carbamoylmethyl-, m.p. 75°–76°.

EXAMPLE 9

Analogously to Example 1, 2-butyl-3-(2'-N-tert-butylaminosulfonyl-3-fluorobiphenyl-4-methyl)-4,5-dihydro-4-oxo-5-N-butylcarbamoylmethyl-3H-IP ("D") is obtained by reaction of "B" with N-butylchloroacetamide. By removal of the tert-butyl group from "D" and reaction with 4-methylpentanoyl chloride, 2-butyl-3-(2'-(4-methylpentanoylaminosulfonyl)-3-fluorobiphenyl-4-ylmethyl)-4,5-dihydro-4-oxo-5-N-butylcarbamoylmethyl-3H-IP, $M^+$=680; Rf 0.54, is obtained.

EXAMPLE 10

Analogously to Example 1, 2-butyl-3-(2'-N-tert-butylaminosulfonyl-3-fluorobiphenyl-4-ylmethyl)-4,5-dihydro-4-oxo-5-piperidinocarbonylmethyl-3H-IP is obtained by reaction of "B" with piperidino-N-carbonylmethyl chloride. 2-butyl-3-(2'-benzyloxycarbonylaminosulfonyl-3-fluorobiphenyl-4-ylmethyl)-4,5-dihydro-4-oxo-5-piperidinocarbonylmethyl-3H-IP, m.p. 173°–174°, is obtained therefrom by removal of the tert-butyl group and reaction with benzyl chlorocarbonate.

Analogously, by reaction of "B" with the appropriate halides (e.g. N,N-diethylchloroacetamide), the 2-butyl-3-(2'-(N-tert-butylaminosulfonyl)-3-fluorobiphenyl-4-ylmethyl)-4,5-dihydro-4-oxo-5-$R^4$-3H-IP compounds below are obtained in which $R^4$ is:
-N,N-diethylcarbamoylmethyl-
-N,N-dimethylcarbamoylmethyl-
-N-tert-butylcarbamoylmethyl-
-N-butylcarbamoylmethyl-
-N-propylcarbamoylmethyl-
-N-(2-methylpropyl)carbamoylmethyl-
therefrom the 2-butyl-3-(2'-aminosulfonyl-3-fluorobiphenyl-4-ylmethyl)-4,5-dihydro-4-oxo-5-$R^4$-3H-IP compounds below in which $R^4$ is:
-N,N-diethylcarbamoylmethyl-
-N,N-dimethylcarbamoylmethyl-
-N-tert-butylcarbamoylmethyl-
-N-butylcarbamoylmethyl-
-N-propylcarbamoylmethyl-
-N-(2-methylpropyl)carbamoylmethyl-
-N-(3-methylbutyl)carbamoylmethyl-,
and therefrom with benzyl chlorocarbonate the 2-butyl-3-(2'-benzyloxycarbonylaminosulfonyl-3-fluorobiphenyl-4-ylmethyl)-4,5-dihydro-4-oxo-5-$R^4$-3H-IP compounds below, in which $R^4$ is:
-N,N-diethylcarbamoylmethyl-
-N,N-dimethylcarbamoylmethyl-
-N-tert-butylcarbamoylmethyl-
-N-butylcarbamoylmethyl-
-N-propylcarbamoylmethyl- -N-(2-methylpropyl)carbamoylmethyl-
-N-(3-methylbutyl)carbamoylmethyl-,

EXAMPLE 11

Analogously to Example 8, by reaction of "C" with the appropriate halides the 2-propyl-3-(2'-(N-tert-butylaminosulfonyl)-3-fluorobiphenyl-4-ylmethyl)-4,5-dihydro-4-oxo-5-$R^4$-3H-IP compounds are below obtained in which $R^4$ is:
-N,N-diethylcarbamoylmethyl-
-N,N-dimethylcarbamoylmethyl-
-piperidino-N-carbamoylmethyl-
-N-tert-butylcarbamoylmethyl-
-N-butylcarbamoylmethyl-
-N-propylcarbamoylmethyl-
-N-(2-methylpropyl)carbamoylmethyl-
-N-(3-methylbutyl)carbamoylmethyl-
therefrom the 2-propyl-3-(2'-aminosulfonyl-3-fluorobiphenyl-4-ylmethyl)-4,5-dihydro-4-oxo-5-$R^4$-3H-IP compounds below in which $R^4$ is:
-N,N-diethylcarbamoylmethyl-
-N,N-dimethylcarbamoylmethyl-
-piperidino-N-carbamoylmethyl-
-N-tert-butylcarbamoylmethyl-
-N-butylcarbamoylmethyl-
-N-propylcarbamoylmethyl-
-N-(2-methylpropyl)carbamoylmethyl-
-N-(3-methylbutyl)carbamoylmethyl-
and therefrom with benzyl chlorocarbonate the 2-propyl-3-(2'-(benzyloxycarbonylaminosulfonyl)-3-fluorobiphenyl-4-ylmethyl)-4,5-dihydro-4-oxo-5-$R^4$-3H-IP compounds in which $R^4$ is:
-N,N-diethylcarbamoylmethyl-
-N,N-dimethylcarbamoylmethyl-
-piperidino-N-carbamoylmethyl-
-N-tert-butylcarbamoylmethyl-
-N-butylcarbamoylmethyl-
-N-propylcarbamoylmethyl-
-N-(2-methylpropyl)carbamoylmethyl-
-N-(3-methylbutyl)carbamoylmethyl-.

The following examples relate to pharmaceutical formulations containing active ingredients of the formula I or their salts.

Example A

Tablets and coated tablets

Tablets of the following composition are produced by compression in conventional manner and, where required, are provided with a conventional sucrose-based coating:

| Active ingredient of the formula I | 100 mg |
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B

Hard gelatin capsules

Conventional two-part hard gelatin capsules are each filled with

| Active ingredient of the formula I | 100 mg |
| Lactose | 150 mg |
| Cellulose | 50 mg |
| Magnesium stearate | 6 mg |

Example C

Soft gelatin capsules

Conventional soft gelatin capsules are filled with a mixture of 50 mg of active ingredient and 250 mg of olive oil in each case.

Example D

Ampoules

A solution of 200 g of active ingredient in 2 kg of propane-1,2-diol is made up to 10 l with water and filled into ampoules so that each ampoule contains 20 mg of active ingredient.

Example E

Aqueous suspension for oral administration

An aqueous suspension of the active ingredient is prepared in conventional manner. The unit dose (5 ml) contains 100 mg of active ingredient, 100 mg of Na carboxymethylcellulose, 5 mg of Na benzoate and 100 mg of sorbitol.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. An imidazopyridine compound of the formula I

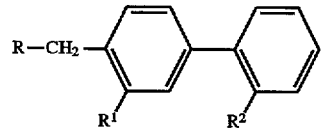

wherein
R is

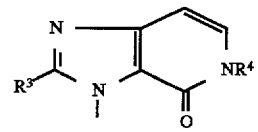

$R^1$ is F,
$R^2$ is —$SO_2NH$—$COR^5$,
$R^3$ is A,
$R^4$ $C_nH_{2n}$—CO—$NR^6R^7$,
$R^5$ is A, —$C_r$—$C_{2r}$-($C_3$-$C_8$-cycloalkyl), $C_rH_{2r}$—Ar, —OA, —O—$C_rH_{2r}$-($C_3$-$C_8$-cycloalkyl), —O—$C_rH_{2r}$—Ar, —$C_pH_{2p}$—(O-$C_3$-$C_8$-cycloalkyl) or —$C_pH_{2p}$—O—Ar,
$R^6$ and $R^7$ are each H, A, or Ar$C_nH_{2n}$, $R^6$ and $R^7$ together are also an alkylene chain having 2–5 atoms, A is $C_1$–$C_6$-alkyl, Ar is an unsubstituted phenyl group, t is 0, 1, 2 or 3, n is 1, 2, 3, 4 or 5, and p is 1 or 2, or a salt thereof.

2. A compound according to claim 1, wherein $R^5$ is —$C_tH_{2t}$-($C_3$–$C_8$-cycloalkyl) or —$C_tH_{2t}$—Ar.

3. A compound according to claim 1, wherein $R^5$ is —$CH_2CH_2$-cyclopenthyl or —$CH_2CH_2C_6H_5$.

4. A compound according to claim 1, wherein $R^4$ is —$CH_2$—CO—$NR^6R^7$, wherein $R^6$ and $R^7$ are each H, A or phenyl.

5. A compound according to claim 1, wherein $R^4$ is —$CH_2CO$—$NR^6R^7$, wherein $R^6$ and $R^7$ together are an alkylene chain having 2–5 C atoms.

6. A compound according to claim 1, which is 2-Butyl-3-(2'-(3-phenylpropionylaminosulfonyl)-3 fluorobiphenyl-4-ylmethyl)-4,5-dihydro-4-oxo-5-N,N-dimethylcarbamoylmethyl-3H-imidazo[4,5-c]pyridine.

7. A pharmaceutical composition comprising a compound of formula I according to claim 1, or one of its physiologically acceptable acid addition salts, and a pharmaceutically-acceptable excipient.

8. A pharmaceutical composition comprising a compound of formula I according to claim 6, or one of its physiologically acceptable acid addition salts, and a pharmaceutically-acceptable excipient.

9. A method of treating or preventing cardiac insufficiency and organ damage associated with hypertension comprising, administering to a host in need thereof, an effective amount of a compound according to claim 1.

10. A method of treating or preventing aldosteronism comprising, administering to a host in need thereof an effective amount of a compound according to claim 1.

11. A method of treating or preventing increased intraocular pressure comprising administering an effective amount of compound according to claim 1.

* * * * *